United States Patent [19]
Zuccato

[11] Patent Number: 5,855,848
[45] Date of Patent: Jan. 5, 1999

[54] CENTRIFUGE APPARATUS FOR CARRYING OUT IMMUNOHAEMTOLOGICAL ANALYSIS OF BLOOD AND OTHER BIOLOGICAL LIQUIDS

[75] Inventor: Alessandro Zuccato, Verona, Italy

[73] Assignee: Sanitaria Scaligera S.p.A., Verona, Italy

[21] Appl. No.: 700,481

[22] PCT Filed: Mar. 3, 1995

[86] PCT No.: PCT/EP95/00785

§ 371 Date: Sep. 6, 1996

§ 102(e) Date: Sep. 6, 1996

[87] PCT Pub. No.: WO95/24634

PCT Pub. Date: Sep. 14, 1995

[30] Foreign Application Priority Data

Mar. 7, 1994 [IT] Italy .............................. VR94A000021

[51] Int. Cl.⁶ .............................. G01N 9/30; B01L 3/00
[52] U.S. Cl. .............................. 422/72; 422/64; 422/100; 422/101; 422/102; 436/45; 436/177; 436/180; 210/515; 210/518
[58] Field of Search .............................. 422/72, 64, 100, 422/101, 102; 436/45, 177, 180; 210/515, 518

[56] References Cited

U.S. PATENT DOCUMENTS

| | | | |
|---|---|---|---|
| 4,225,558 | 9/1980 | Peterson et al. | 422/72 |
| 4,226,531 | 10/1980 | Tiffany et al. | 356/246 |
| 4,284,602 | 8/1981 | Kelton et al. | 422/72 |
| 4,456,581 | 6/1984 | Edelmann et al. | 422/72 |
| 4,693,834 | 9/1987 | Hossom | 210/767 |
| 4,714,590 | 12/1987 | Guigan | 422/102 |
| 4,812,294 | 3/1989 | Combs | 422/72 |
| 4,814,144 | 3/1989 | Edelmann et al. | 422/102 |
| 4,832,851 | 5/1989 | Bowers et al. | 210/650 |
| 4,915,847 | 4/1990 | Dillon et al. | 210/737 |
| 4,952,516 | 8/1990 | Matkovich | 436/170 |
| 5,358,690 | 10/1994 | Guirguis | 422/58 |
| 5,610,074 | 3/1997 | Beritashvili et al. | 436/177 |

FOREIGN PATENT DOCUMENTS

| | | |
|---|---|---|
| 0 141 009 | 5/1985 | European Pat. Off. . |
| 0 295 069 | 12/1988 | European Pat. Off. . |
| WO 94/00169 | 1/1994 | WIPO . |

*Primary Examiner*—Harold Y. Pyon
*Attorney, Agent, or Firm*—Evenson, McKeown, Edwards & Lenahan, P.L.L.C.

[57] ABSTRACT

Test tube particularly suitable for carrying out immunological and immunohaematological analysis having at one end thereof an opening for charging reagents and biological liquids to be analyzed and, at the other end thereof, at least one venting opening and a respective controlled-stop filter.

5 Claims, 5 Drawing Sheets

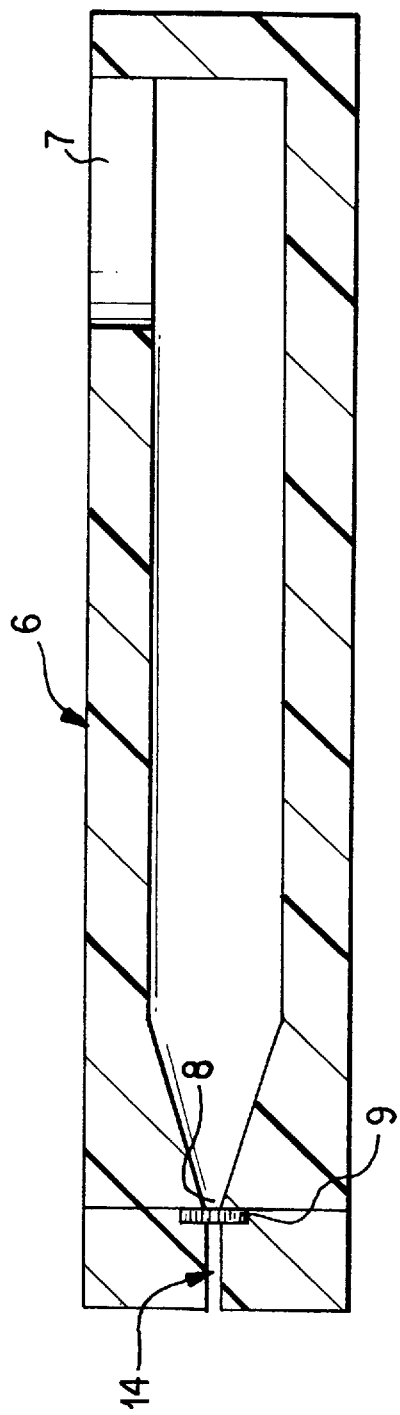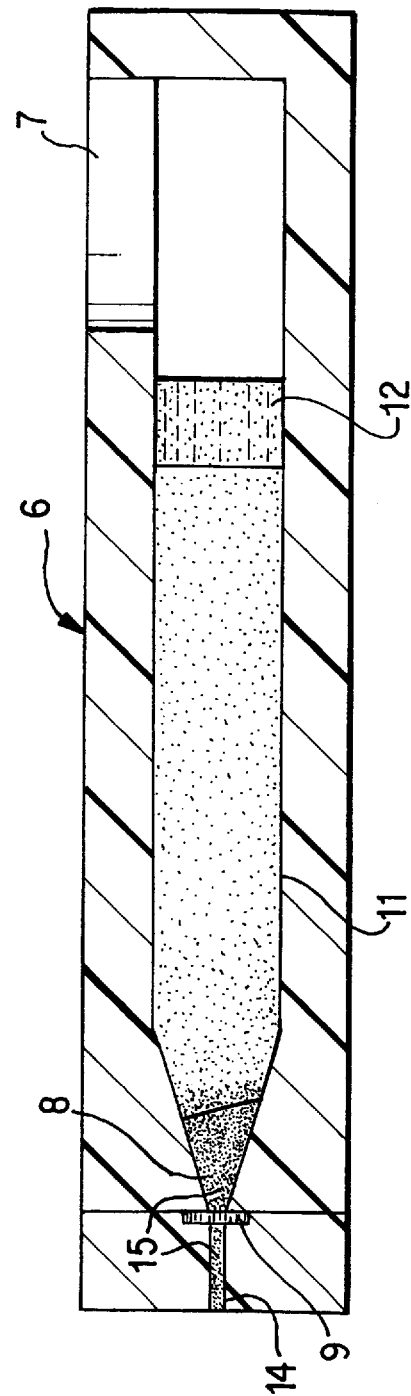

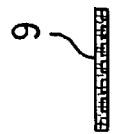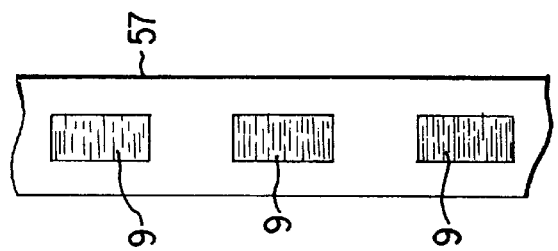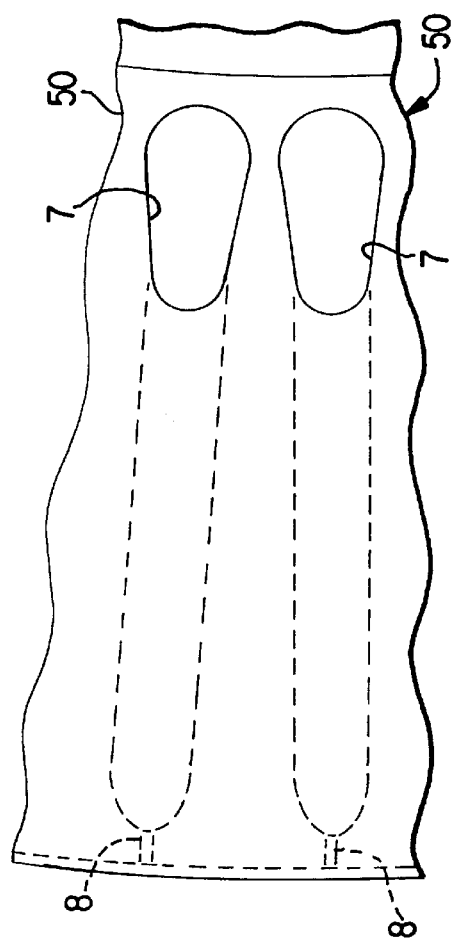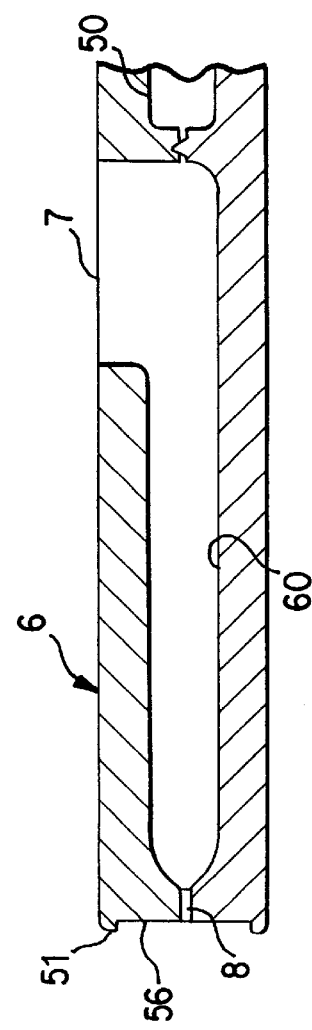

CENTRIFUGE APPARATUS FOR CARRYING OUT IMMUNOHAEMTOLOGICAL ANALYSIS OF BLOOD AND OTHER BIOLOGICAL LIQUIDS

This applicantion is a 371 of PCT/EP95/00785 filed Mar. 3, 1995.

TECHNICAL FIELD

The present invention relates to a centrifuge apparatus for carrying out immunological and immunohaematological analysis and tests on centrifuge.

BACKGROUND ART

As is known, these tests can be carried out according to a number of methods which include the use of specific reagents that once in contact with a biological liquid indicate the presence of sought element or elements in it.

Depending upon the type of research and reagent used, the operator will follow methods which differ in length, handling, quantity of reagent to be used and biological liquid to be put in reaction.

For instance, one of the methods most commonly used to determine the blood group of a person includes causing a reaction between blood of that person and an inert substance comprising microgranules of a synthetic material having various diameters hereinafter called "gel" for convenience, and a specific antiserum for the sought antigen.

More particularly, the method used in this case is the following:

- a known quantity of gel, to which a specific antiserum for the test to be carried out has been homogeneously added in advance, is placed inside a glass or plastic test tube,
- a determined quantity of suitably diluted red globules to be tested is added in the same test tube,
- the test tube is located in a centrifuge to allow the red blood globules to mix with the solution previously placed in the test tube, and
- should the red globules react with the antiserum in the tube while being centrifugated, they form agglutinates, whereas the gel prevents them from sedimenting at the bottom of the test tube,
- should the reaction be optically positive, i.e. should the red blood globules react with the antiserum, no formation of a well defined "button" will occur at the bottom of the test tube, and dispersion of the agglutinates in the solution of the gel located on top will take place.

Another method used is that concerning the "Coombs test" and crossed tests.

In that case, the followed method comprises the following steps:

- a known quantity of gel is placed inside a glass or plastic test-tube in which Coombs serum was homogeneously added in advance,
- a determined quantity of "haemacies", i.e. panantigenic red globules including all the known antigens in their structure, is added to the same test-tube,
- a specific quantity of serum to be tested is added to the same test tube,
- the contents in test tube are then left to incubate for a time interval ranging from 10 to 15 minutes,
- after incubation the test tube is placed in a centrifuge to be centrifugated at a predetermined speed.

If during incubation and centrifugation steps a reaction has taken place, the result will be agglutination between "haemacies", serum to be tested and Coombs serum.

Also in this case, the gel prevents the agglutinates from forming a well defined "button" in the test tube.

Devices ready for use are available on the market which comprises a series of test tubes (usually six or eight in number that are placed one next to the other and connected to each other by a single plastic support), in which gel (i.e. a support substance for the reaction) suitably mixed with the reagent (such as antiserum, Coombs serum, or another serum) was previously added.

These devices have the definite advantage of offering the operator a device ready for use for carrying out tests, i.e. the test tube does not require to be filled with gel and reagent by the operator, since it is already loaded with such components.

There are, however, numerous disadvantages among which the pre-configuration of the tests. As a matter of fact, the manufacturers of these devices ready for use must necessarily foresee two things: a mininum number of already loaded test tubes to be included in the same device or system—hereinafter called "index card" for convenience—and a given configuration of tests to be carried out on the index card.

A frequent inconvenience of this state of affairs is to be faced when the operator has to carry out only three blood tests, but is going to use an index card which has six or eight test tubes ready for use, and thus he is not going to use more than half of the test tubes available, while the rest are to be disposed unused.

If one takes into account the great number of blood tests (anti-A, anti-B, anti-E, etc.) which are carried out, one will realize that substantial waste occurs, this being especially true in those centers where only relatively few blood tests are carried out.

An alternative solution would be that the operator should wait to carry out blood tests until he has gathered a number of tests at least approximately equal to that or a multiple of the available test tubes in an index card.

Another disadvantage of the "index card" lies in the difficulty in automating the testing procedure described above.

Bearing in mind that several working steps are involved, i. e. introduction of various liquids into the test tubes of an index card, incubation, centrifugation and surveying and reading the test results, a complex and expensive equipment is required.

Document EP-A-0295069 discloses a diagnostic test device for detecting the presence of a component in a liquid sample, comprising a liquid impervious receptacle vented by a liquofobic element. The receptacle houses an absorbent which contacts and draws liquid through a microporous reaction medium, gas being displaced from the absorbent during the liquid absorption.

Document EP-A-0141009 discloses a rotor unit of a centrifugal analyser. The rotor unit is divided into several different elements, each of these elements containing felt members and a pre-packaged reagent which, during the rotation of the rotor unit, is mixed up with the testing sample into a measuring room. The optical absorption measurement is carried out by means of a polychromatic photometer.

Document U.S. Pat. No. 4,226,531 discloses a disposable multi-cuvette rotor for use in an analytical photometer which comprises two injection molded parts from a transparent material of suitable chemical and absorption characteristics. Each of the cuvettes is divided into adjoining sample and reagent/measuring chambers by a wedge-shaped element.

DISCLOSURE OF THE INVENTION

The main object of the present invention is to obviate or substantially eliminate the disadvantages referred to above in connection with known devices and systems, by providing a centrifuge apparatus for carrying out immunological and immunohaematological tests in relatively short time intervals without manual intervention of the operator and with no waste of reactive material.

A further objest of the present invention is to provide a centrifuge apparatus provided with a test tube which relatively simple in structure, and thus fully reliable in operation and inexpensive to manufacture.

This is achieved by a centrifuge apparatus having the features disclosed in claim 1.

The dependent claims outline advantageous forms of embodiment of the centrifuge apparatus according to the invention.

BRIEF DESCRIPTION OF THE DRAWINGS

Further features and advantages of the present invention will better appear from the following detailed description of preferred embodiments thereof, given by way of non limiting examples and illustrated in the accompanying drawings in which:

FIGS. 2a and 2b show details in side view of a test tube;

FIG. 6 is a top view showing a detail of the plate of FIG. 4 in an enlarged scale;

FIG. 7 is a cross-section view taken along lines VII—VII of FIG. 6;

FIG. 8 shows a section of a self-adhesive filter bearing strip for use in connection with a platform or plate of FIG. 4; and FIG. 9 is a side view of the filter bearing strip of FIG. 8.

WAYS OF CARRYING OUT THE INVENTION

Figure 1:
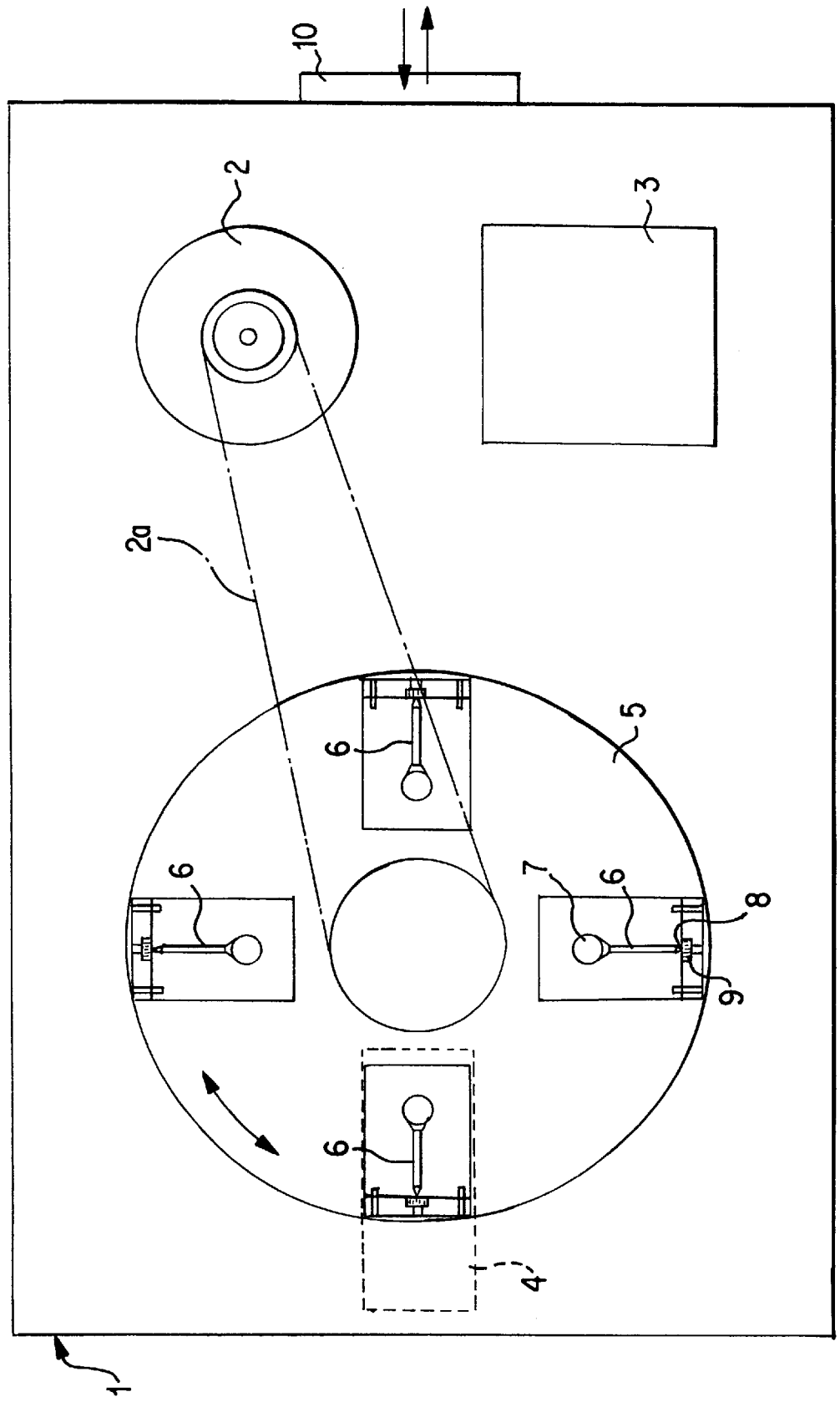
FIG. 1 shows a schematic view from above of the testing apparatus according to the present invention.

In the accompanying drawings the same reference numerals have been used to indicate the same or the like components.

Figure 3:
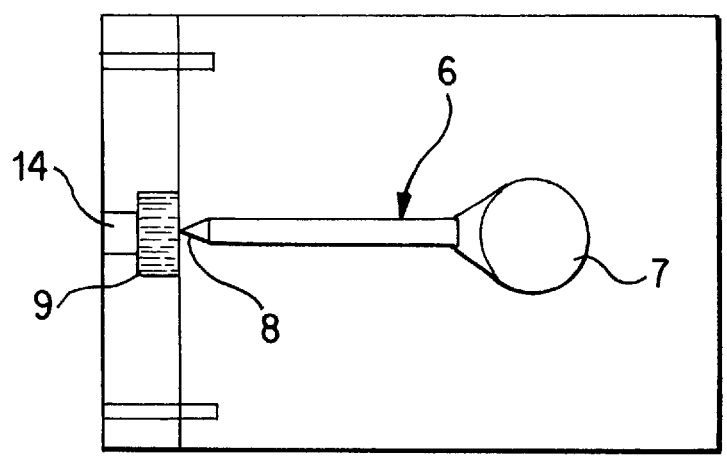
FIG. 3 shows a detail from a view from above of a test tube seated in the testing apparatus of FIG. 1.

With reference first to FIGS. 1 to 3, an apparatus for carrying out immunological and immunohaematical tests is generally indicated at 1 and includes an electric motor 2, a control system 3 for detecting the number of rotations of the motor 2, an optical colour scanning system 4, a rotating platform or plate 5 revolving for example around a vertical axis, and test tubes 6 made of a transparent material. Each test tube 6 has an opening 7 for loading liquids in it, and a venting hole 8 for discharging air from the test tube and a microporous filter 9 at or in hole 8. A computer 10 is arranged to control analogical and digital functions.

The electrical motor 2 can be of any suitable kind and through a transmission, e.g. a transmission belt 2a, causes the test tube carrying plate 5 to rotate in clockwise or anticlockwise direction at a predetermined rotation speed.

The control system 3 can be of any suitable type and makes it possible to constantly control by means of a computer 10 the angular position taken by the test tube carrying platform or plate 5 with respect to a predetermined reference position.

The colour reading system 4 can be a scanner of any suitable type and allows the computer 10 to read and elaborate the images of the reactions occurred in each test tube 6 supported by the plate 5.

The test tube bearing plate 5 can have any other suitable form, e.g. it can be circular in shape, and supports a predetermined number of test tubes 6, such as four test tubes.

Each test tube 6, as is better shown in FIGS. 2a, 2b, and 3, is designed to contain gel+reagent 11 and a biological liquid 12. As specified above, each test tube has, at one end thereof, an aperture 7 for the introduction of gel plus reagent 11 and of the biological liquid 12, and a hole 8 at its other end far from the aperture 7. designed to allow air 15 being displaced by the introduction of materials 11 and 12 to be vented, as well as a microporous filter 9 located in such a way as to intercept the hole 8 to allow the air 15 to be discharged through a venting channel 14, but retaining the reagent and the gel 11 as well as the biological liquid 12 in the test tube. The diameter of the pores of the filter is selected so as to retain the material constituted by the gel+reagent, but it allows air to pass through. A suitable material for a microporous filter 9 is, for example, a textile material commercially known as GORETEX, produced by the Goretex Inc.—USA.

For a better understanding of the way in which an haematological test can be carried out by making use of the above described apparatus, reference should be made in particular to FIGS. 1, 2a, 2b.

With a dispensing machine of any suitable type for the reagents, first of all a determined quantity of gel+reagent 11 is loaded in a test tube 6, which is located in a respective radial seat 60 provided in a test tube bearing plate 5 (FIG. 1) in such a way that its venting hole 8 is adjacent to the outer peripheral part of the plate. The motor 2 is then energized and thus it sets the test tube bearing plate 5 in rotation at a number of turns per time unit detected by the encoder 3 and program-controlled by the computer 10, so as to allow the gel+reagent material 11 to be uniformly distributed inside the test tube 6, while any air in the test tube being expelled in order to avoid the formation of air bubbles inside the material 11.

The air inside the test tube 6 is actually forced to leave completely the test tube 6, initially owing to the "mechanic" displacement of the loaded material 11 and subsequently owing to centrifugal effect. The gel+reagent material 11 has sufficient consistency to form a material barrier to the air 15, which cannot enter the material 11, where it might give rise to the formation of bubbles. Thus, the air is forced to pass through the filter 9 to be discharged outside along the channel 14.

The apparatus 1 comprises an optical reader 4 arranged opposite the end of the test tube 6, where its hole 8 is located or in any other suitable place where no problems in detecting the results of the test occur.

Rotation of the test tube carrying plate 5 is automatically brought to an end by the computer 10.

The dispensing machine for reagent delivery will then load each test tube 6 through its aperture 7 with a suitable amount of biological liquid 12 to be analyzed.

The test tube bearing plate 5 will be again rotated at a number of turns controlled by the encoder 3 and the computer 10, so that the biological liquid 12 can react with the gel+reagent 11.

As soon as the reaction is terminated, the rotation of the test tube carrying plate 5 is stopped and a reading phase by scanner 4 is started. The test tube bearing plate 5 is caused to rotate slowly by the electric motor 2, which is constantly controlled by the encoder 3 and the computer 10, so that a complete scanning of the surface of each test tube on the test tube bearing plate 5 can be executed.

The computer 10 will then process the data from the scanner 4 and, by taking advantage of a suitable software for image composition, shall display the result of the reaction which has occurred inside the test tube 6.

Figure 5:
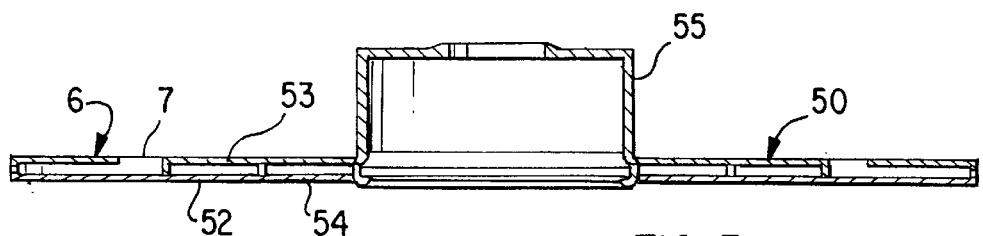
FIG. 5 is a cross-section view taken along lines V—V of the rotating platform of FIG. 4.
Figure 4:
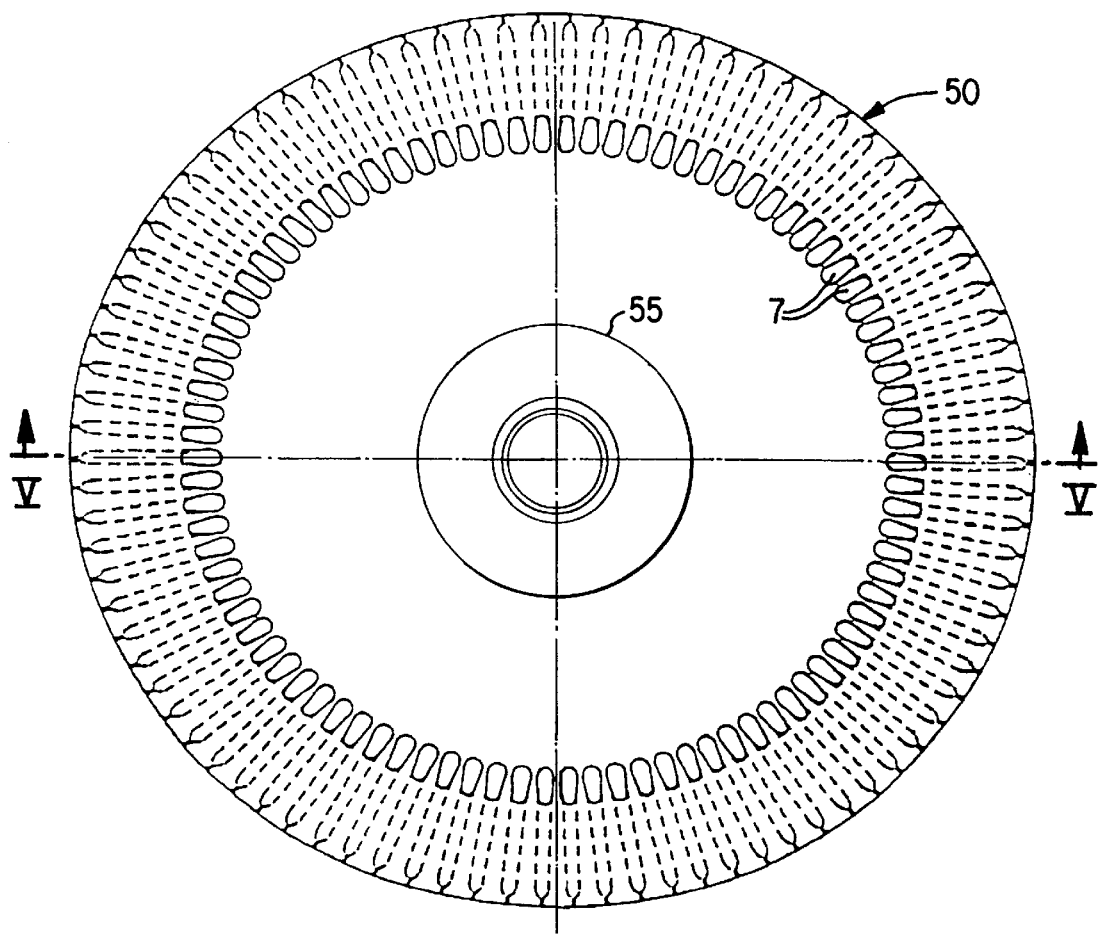
FIG. 4 is a top view of another embodiment of rotating platform or plate.

FIGS. 5 to 9 illustrate a further embodiment of test tube bearing plate or platform 50 which is provided with a large number, e.g. 90, radially estending test tubes 6, each of which has an aperture 7 for loading in it gel+reagent material 11 and biological liquid 12 by means of a dispensing machine, as well as a venting hole or duct 8 at its peripheral border 51. The plate 50 can be obtained by joining together, e.g. by ultrasonic welding, two shells 52 and 53 each having a number of matching and spacing ribs 54 (FIG. 5). An axial hub 55 may be provided on the plate 50 for a stabler mounting on a vertical rotating mandrel—not shown in the drawings—of the testing apparatus 1.

The plate 50 is formed with a peripheral uninterrupted groove 56 with which every hole 8 communicates. A strip 57 of suitable (self-adhesive) material bearing a number of filters 9 arranged at a distance from each other corresponding to the angular distance between two successive venting holes 8, can be applied along the groove 56, so that each hole 8 is intercepted by a respective filter 9.

Each time the operator either utilizes all the test tubes 6 or only a number thereof, the remaining test tubes 6 being at disposal for subsequent tests, until all the test tubes in the plate 50 are used.

Of course, instead of numerous filters 9 on the strip 57, one can provide a continuous web of textile material 9.

I claim:

1. A centrifuge apparatus comprising at least one test tube, said test tube having an elongate shape and comprising, at a first end thereof, a loading aperture through which a reagent and a biological liquid is loaded into said test tube and, at the other end thereof, a venting duct which is closed by a microporous filter allowing passage of air through said opening while retaining any liquid and/or solid material inside of said test tube during operation of said centrifuge apparatus, said centrifuge apparatus comprising a rotor plate on which said at least one test tube is radially supported.

2. Apparatus according to claim 1 in which each said test tube is at least partially made of a transparent or translucent material in order to allow the whole test tube length to be scanned by an image scanning device.

3. A non-invasive method of carrying out immunological and immunohaemotological tests using an apparatus according to claim 1 and comprising the following steps:

loading a gel and a reagent material or materials into the test tube or tubes of an apparatus according to claim 1, through the or each respective loading aperture;

carrying out a first centrifugation operation, in order to uniformly distribute the gel and the reagents within the test tube(s) and to exhaust the air through said venting duct;

loading a biological liquid to be tested through the or each respective loading aperture;

carrying out a second centrifugation operation until test reaction between reagents and said biological liquid is completed;

carrying out an optical scanning of each test tube, followed by processing of the scanning signals.

4. Apparatus according to claim 1, wherein said at least one test tube is supported on said rotor plate to extend radially thereon.

5. Apparatus according to claim 1, wherein a plurality of test tubes are supported on said rotor plate extending radially therein.

* * * * *